(12) United States Patent
Cancel et al.

(10) Patent No.: US 6,428,546 B1
(45) Date of Patent: Aug. 6, 2002

(54) APPARATUS FOR THE INSTALLATION OF A PROSTHESIS IN THE TREATMENT OF INGUINAL HERNIAS VIA THE PERITONEOSCOPIC ROUTE

(76) Inventors: Richard Cancel, 317, rue Olive Tamari, F-83130 La Garde; Richard Wallace, 18, rue du Paradis, F-83400 Hyeres; Gérard Sassi, 105, boulevard Coste Chaude, F-83200 Toulon, all of (FR)

( * ) Notice: Subject to any disclaimer, the term of this patent is extended or adjusted under 35 U.S.C. 154(b) by 0 days.

(21) Appl. No.: 09/578,885

(22) Filed: May 26, 2000

Related U.S. Application Data

(63) Continuation of application No. PCT/FR98/02559, filed on Nov. 27, 1998.

(51) Int. Cl.[7] .................................................. A61F 11/00
(52) U.S. Cl. ........................................ 606/108; 606/151
(58) Field of Search ........................... 606/108, 14, 196, 606/151; 604/14; 600/219, 206

(56) References Cited

U.S. PATENT DOCUMENTS

| | | | | |
|---|---|---|---|---|
| 3,783,873 A | * | 1/1974 | Jacobs | 606/151 |
| 4,869,268 A | * | 9/1989 | Yoon | 128/831 |
| 5,383,477 A | * | 1/1995 | DeMatteis | 128/898 |
| 5,395,383 A | * | 3/1995 | Adams et al. | 606/151 |
| 5,397,332 A | | 3/1995 | Kammerer et al. | 606/151 |
| 5,405,360 A | * | 4/1995 | Tovey | 606/151 |

FOREIGN PATENT DOCUMENTS

| | | |
|---|---|---|
| EP | 0 557 963 A1 | 9/1993 |
| EP | 0 557 964 A1 | 9/1993 |
| EP | 0 625 334 A1 | 11/1994 |
| EP | 0 706 778 A1 | 4/1996 |
| WO | WO 92/06338 | 4/1992 |

\* cited by examiner

*Primary Examiner*—John J. Wilson
*Assistant Examiner*—Melba Bumgarner
(74) *Attorney, Agent, or Firm*—Schnader Harrison Segal & Lewis LLP

(57) ABSTRACT

The invention provides an apparatus enabling the introduction of a prosthesis of the pad form with increased ease into the interior of the abdominal cavity and to automatically unroll it, such that its installation and stapling are easier for the practitioner. More specifically, the invention includes a device for the installation of a prosthesis in the treatment of inguinal hernias via peritoneoscopy, including an applicator essentially constituted of a substantially cylindrical tube capable of containing the prosthesis, a plunger for injecting the prosthesis from the tube at the desired site, and a spring attached to the plunger such that it is capable of attaching to the prosthesis in a detachable manner and of spreading it out when it is discharged to the exterior of the tube.

10 Claims, 3 Drawing Sheets

APPARATUS FOR THE INSTALLATION OF A PROSTHESIS IN THE TREATMENT OF INGUINAL HERNIAS VIA THE PERITONEOSCOPIC ROUTE

RELATED APPLICATIONS

This is a continuation of International Application No. PCT/FR98/02559, with an international filing date of Nov. 27, 1998, which is based on French Patent Application Nos. 97/15027 filed Nov. 28, 1997 and 98/01277 filed Feb. 4, 1998.

FIELD OF THE INVENTION

This invention pertains to the treatment of inguinal hernias via the peritoneoscopic route. More specifically, the invention relates to apparatus for the installation of a prosthesis in the abdominal cavity in the implementation of this treatment.

BACKGROUND

Inguinal hernias result from the passage of intra-abdominal organs to the outside of the abdominal cavity, passing through the muscular wall. This abnormal passage stems from a defect which can be congenital or acquired. Inguinal hernias are very common disorders, such that surgical interventions for repairing these defects are at present among the most frequently performed operations.

There are two problems related to the repair of inguinal hernias: their frequency and the rate of recidivism after treatment. An imperfect operative technique results in a high recidivism rate with the associated human and social consequences (repeated surgical interventions, increased costs).

There has been an ongoing attempt to improve the surgical techniques applied to the treatment of inguinal hernias to decrease the recidivism rate and, above all, to allow patients to resume their social and professional activities as quickly as possible.

It turns out that in the majority of acquired hernias, the most reliable treatment involves installation of a prosthesis, i.e., an element made of a foreign material which, by inducing intense fibrosis, is the agent of repair. The problems associated with the prosthetic material entail its tolerance as well as its installation. Considerable progress has already been achieved both with regard to the material used for the prosthesis as well as its installation. The peritoneoscopic route is the least invasive possible technique as well as the best tolerated.

At present, the prosthetic material is installed via the peritoneoscopic route by introduction inside a trocar. Although this represents definite progress for the patient as well as for the surgeon, it is undeniable that the existing systems still have drawbacks.

Because the conventional dimension of the prosthesis is typically 13×10 cm, it is necessary to roll the prosthetic element like a cigarette to be able to introduce it via a trocar. It is tedious to have to unroll this element after it has been introduced into the interior of the abdominal cavity and then to maintain it in the correct position so that it can be stapled. Thus, it would be advantageous to provide an apparatus which facilitates the introduction, installation and stapling of such an element inside the abdominal cavity.

SUMMARY OF THE INVENTION

This advantage is attained according to the invention which provides an apparatus enabling the introduction with increased ease of a prosthesis of the previously mentioned type in pad form into the interior of the abdominal cavity and to automatically unroll it, such that its installation and stapling are easier for the practitioner. More specifically, the invention includes a device for the installation of a prosthesis in the treatment of inguinal hernias via peritoneoscopy, comprises:

an applicator essentially constituted of a substantially cylindrical tube capable of containing the prosthesis and of a plunger for injecting the prosthesis from the tube at the desired site, and a spring attached to the plunger such that it is capable of attaching to the prosthesis in a detachable manner and of spreading it out when it is discharged to the exterior of the tube.

DETAILED DESCRIPTION OF THE INVENTION

Figure 1:
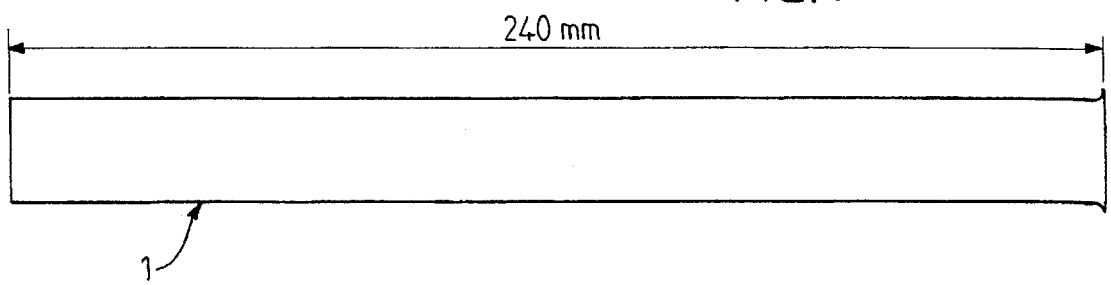
FIG. 1 shows schematically a tube which can be used as the applicator according to the invention.

It will be appreciated that the following description is intended to refer to specific embodiments of the invention selected for illustration in the drawings and is not intended to define or limit the invention, other than in the appended claims.

Figure 2A:
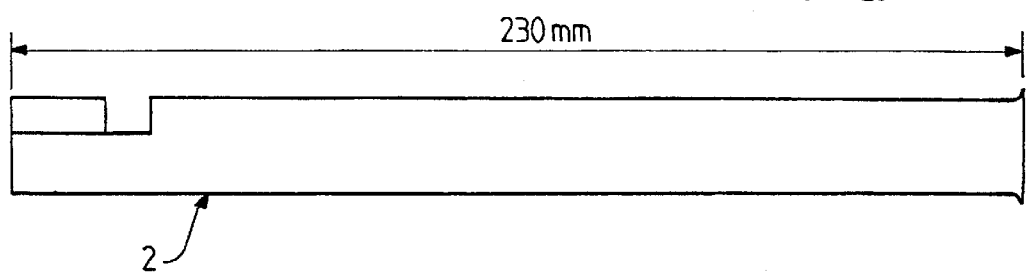
FIGS. 2a, 2b and 2c show schematically, in front, cross-sectional and top views, respectively, a plunger which can be used for the applicator according to the invention.
Figure 2B:
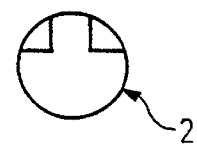
Figure 2C:
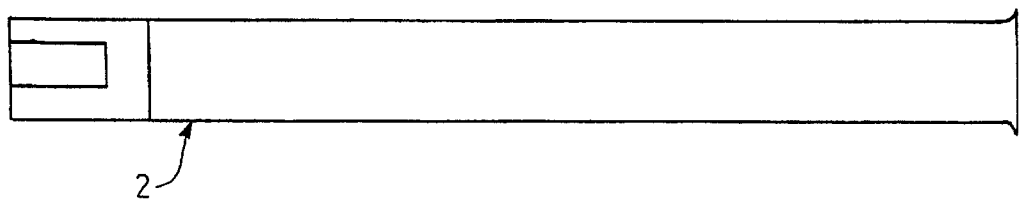
Figure 3:
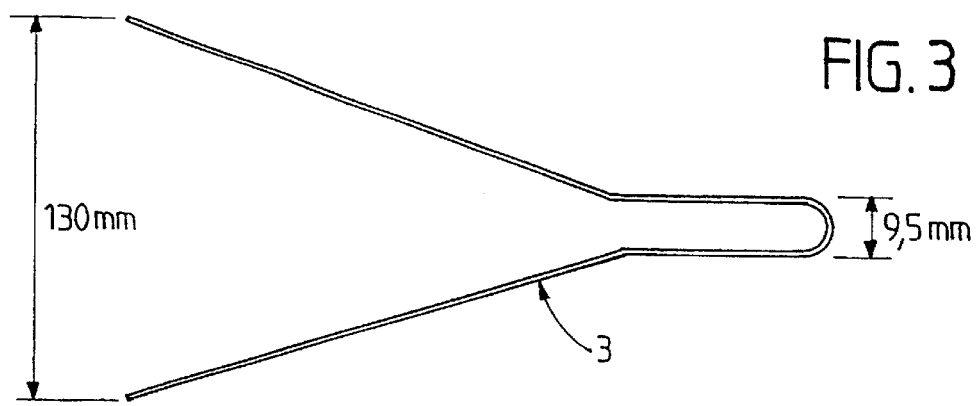
FIG. 3 shows a spring which can be used according to the invention.
Figure 4:
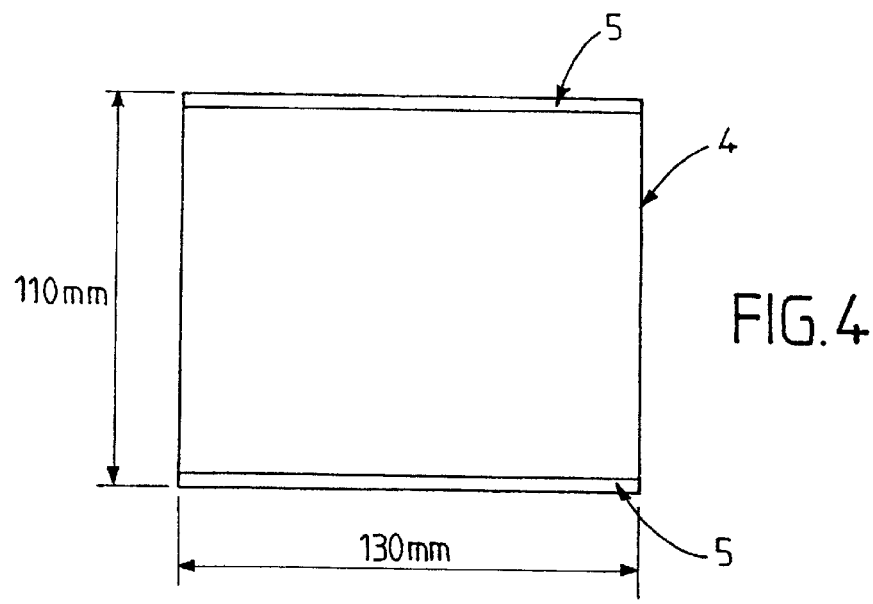
FIG. 4 shows a flexible, square pad intended to constitute the prosthesis and provided with loops into which can be introduced, in a detachable manner, the rectilinear parts of the spring shown in FIG. 3.

Turning now to the drawings in general and FIG. 1 in particular the tube 1 is made of a rigid material such as polyvinyl chloride (PVC), stainless steel (304) and the like. The outside diameter of tube 1 depends on the size of trocar that will be used and its inside diameter which will receive plunger 2, spring 3 and flexible pad or prosthesis 4 rolled around itself. These are shown in FIGS. 2–4. Similarly, the length of the tube is selected so as to be able to receive these various elements. Typically, tube 1 has a length of about 240 mm and an outside diameter of about 10 mm, preferably 10–12 mm. As shown in FIG. 1, one end of tube 1 has a safety means, for example, a flange, preventing the tube 1 from penetrating too deeply the trocar when it is used.

Figure 5A:
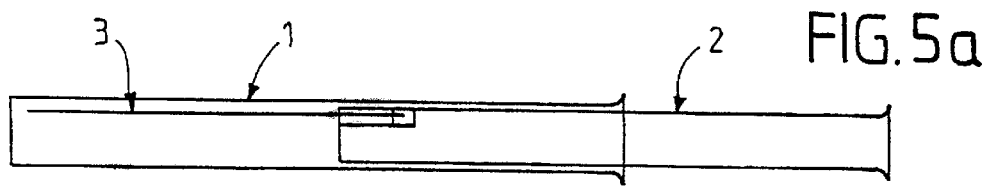
FIGS. 5a and 5b show schematically, in front and top views, respectively, a mode of implementation of the device according to the invention comprising the elements from FIGS. 1 to 3 before the plunger is inserted into the tube.
Figure 5B:
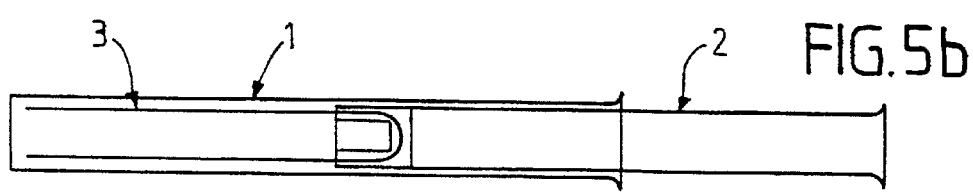
Figure 6:
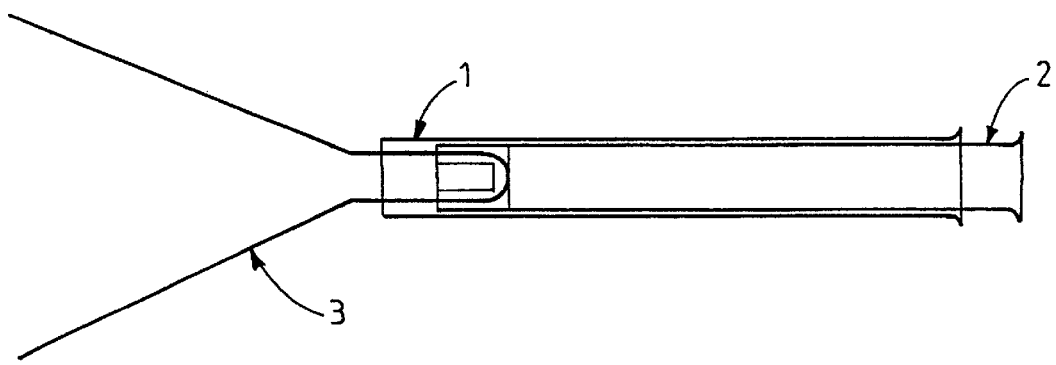
FIG. 6 shows the device of FIG. 5b with the plunger inserted.
Figure 7:
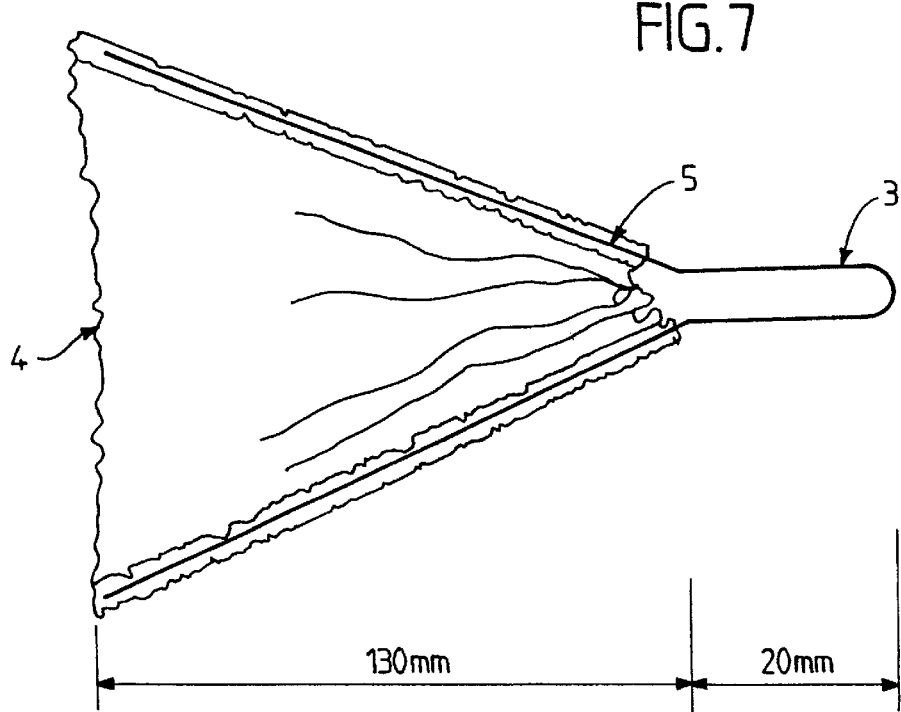
FIG. 7 shows the spring of FIG. 3 with its rectilinear parts introduced into the loops of the partially spread out pad of FIG. 4.

Plunger 2 is made of a rigid material such as polyvinyl chloride (PVC) and the like. Its outside diameter is such that it can slide without substantial resistance inside tube 1. Its length is close to that of tube 1. Typically, plunger 2 has a length of about 230 mm and an outside diameter of about 10 mm, preferably 3–12 mm for travel within the tube 1. As shown in FIGS. 2, 5 and 6, one end of plunger 2 is provided with a means allowing it to be pushed or pulled. The other end is provided with a means enabling attachment of spring 3 to fasten it to plunger 2.

Spring 3 is made of a biocompatible metal or metallic alloy, preferably stainless steel, and designed such that it enables the spreading out of flexible pad or prosthesis 4 when it is relaxed.

Pad 4 intended to constitute the prosthesis is made of a biocompatible material that is sufficiently lacunary or porous so as to support in vivo tissue implantation or growth and sufficiently flexible so as to be rolled up on itself and unrolled. This material is preferably a textile produced by weaving and/or knitting and/or injection of a resin of polypropylene, polyamide, polyester and the like. Pad 4 is provided with means to receive spring 3, such as, for example, loops 5, rings, meshes and the like. Typically, pad 4 has the dimensions about 110×130 mm, but other dimensions can be provided depending on the user's needs.

Thus, using the same installation device (tube 1 of length from about 150 to 300 mm, of inside diameter from about 2 to 15 mm and of outside diameter from about 3 to 12 mm, typically about 5 mm; plunger 2 of length from about 150 to 300 mm and of outside diameter from about 2 to 15 mm; rectilinear parts of spring 3 from about 8 to 250 mm), the pad can be rectangular or square with, for example, the following dimensions:

1. 15×13 cm (the most common size),
2. 15×13 cm,
3. 13×13 cm, or
4. have another shape with a cut-out The prostheses of types 1 to 3 are usually used for the transperitoneal peritoneoscopic route, which is the conventional peritoneal surgery route.

On the other hand, the prosthesis of type 4 with cut-out provided so as to allow passage of the cord (anatomical element which connects the testicle to the inside of the abdominal cavity, passing through the wall, which constitutes the point of weakness) around the pad, is usually used for the preperitoneal or subperitoneal route by means of which one passes between the peritoneum and the muscular wall, i.e., to the exterior of the abdominal cavity or the route by laparotomy.

The applicator which comprises tube 1 and plunger 2 allows injection of pad or prosthesis 4 at the desired site. When pad 4—attached to spring 3—is pushed to the outside of tube 1 by means of plunger 2, it unrolls outside of tube 1, at its end, under the effect of the relaxation of spring 3, to which it had been attached before the injection.

A stapler introduced via the contralateral trocar allows attachment of pad 4 first at the level of the bone (Cooper's ligament) and then to staple it towards the top without it being necessary to manipulate it because it is maintained in the correct position by means of spring 3.

Use of such a spring according to the invention considerably facilitates the practitioner's work because he no longer has to unroll the pad and then maintain it in the correct position for stapling. According to the invention, the spring itself perform these two functions.

After the two stapling operations explained above have been performed, the device according to the invention comprising tube 1 and plunger 2, attached to spring 3, is progressively withdrawn so as to release pad 4.

Finally, when the pad is completely released from the device because it has been entirely withdrawn, the part of the pad that had remained in the tube is now stapled in its vertical part.

The correct stapling of pad or prosthesis 4 implemented in this manner makes it possible to completely avoid stapling this prosthesis towards the bottom, which can be the source of painful postoperative problems.

The device according to the invention allows the prosthesis to be spread out on solely two arms of the spring. This device is fundamental because it allows the progressive release of the prosthesis as stapling is performed. In addition, as the device is withdrawn, the pad is progressively released and liberated in good position so as to allow the possibility of immediate stapling in its definitive position. This spring is not only an introduction presentation device but also a device for the installation of the prosthesis in its definitive position.

Advantageously, the device according to the invention allows introduction of the pad from the ipsilateral side in relation to the hernia to be treated, which allows a much larger clearance for the stapler which is on the side contralateral to the hernia.

In addition, the device allows automatic spreading out of the prosthesis and its installation in definitive position by a single instantaneous and automatic pressure of the thumb on the plunger as would be used with an ordinary syringe.

In addition, the device according to the invention is the only instrument which provides all of these advantages and these innovations in a 5-mm diameter tube comprising the totality of the mechanisms and the prosthesis.

Advantageously, the tube has an outside diameter of about 3 to 12 mm.

This mode of implementation is a preferred variant in that it avoids the implementation of a suture after the intervention. In addition, it allows use of standardized trocars, which reduces the cost of the intervention.

Although this invention has been described in connection with specific forms thereof, it will be appreciated that a wide variety equivalent may be substituted for the specific elements described herein without departing from the spirit and scope of the invention as described in the appended claims.

What is claimed is:

1. Apparatus for the installation of a prosthesis in treating inguinal hernias via peritoneoscopy, comprising:
   an applicator of a substantially cylindrical tube with an outside diameter sized to contain the prosthesis;
   a plunger for the injection of the prosthesis from the tube at a selected site; and
   a spring, comprising only two arms, which spring is attached to the plunger wherein each arm terminates in a free end such that each arm may accept and removably hold the prosthesis along an edge thereof.

2. The apparatus according to claim 1, wherein the cylindrical tube is made of polyvinyl chloride.

3. The apparatus according to claim 1, wherein the cylindrical tube further comprises a safety means at one of its end portions.

4. The apparatus according to claim 1, wherein the plunger is made of polyvinyl chloride.

5. The apparatus according to claim 1, wherein the plunger further comprises a means allowing it to be pushed or pulled.

6. The apparatus according to claim 1, wherein the spring is made of a biocompatible metal or metallic alloy.

7. The apparatus according to claim 1, wherein said spring is made from stainless steel.

8. The apparatus according to claim 1, wherein:
   the tube has a length from about 150 to 300 mm, an inside diameter from about 2 to 15 mm and an outside diameter from about 3 to 12 mm; and the plunger has a length from about 150 to 300 mm and an outside diameter from about 2 to 15 mm, and rectilinear parts of the spring have a length from about 8 to 250 mm.

9. Apparatus for the installation of a prosthesis in treating inguinal hernias via peritoneoscopy comprising:

a substantially cylindrical tube sized to contain the prosthesis prior to installation;

a plunger sized and shaped to slide within the tube for ejecting the prosthesis from the tube, and having a notched portion at an end portion thereof; and a spring having a substantially "U" shaped closed end portion engaging the notched portion and two spring arms, each adapted to removably engage the prosthesis along an edge thereof.

10. The apparatus according to claim 9, wherein the two spring arms are diverging and extending from the "U" shaped portion, the spring arms being pre-tensioned to diverge when ejected from the tube to thereby open said prosthesis into a substantially flat sheet.

* * * * *